United States Patent [19]

Chlosta et al.

[11] Patent Number: 4,554,436
[45] Date of Patent: Nov. 19, 1985

[54] ELECTRIC HEATER FOR A ROTATING SAMPLE VESSEL CONTAINER IN A SAMPLING DEVICE FOR GAS CHROMATOGRAPHY

[75] Inventors: Wolfgang Chlosta, Uberlingen; Wolfgang Riegger, Salem, both of Fed. Rep. of Germany

[73] Assignee: Bodenseewerk Perkin-Elmer & Co., GmbH, Uberlingen, Fed. Rep. of Germany

[21] Appl. No.: 589,821

[22] Filed: Mar. 15, 1984

[51] Int. Cl.[4] ............................................. H05B 3/58
[52] U.S. Cl. .................................... 219/385; 219/535; 219/389; 219/521; 219/549; 432/138; 73/23.1; 55/386; 210/657
[58] Field of Search ............... 219/385, 535, 389, 521, 219/469–471, 549; 73/23.1; 432/138, 11; 165/120; 422/89, 70; 210/657; 55/67, 386, 197

[56] References Cited

U.S. PATENT DOCUMENTS

| | | | |
|---|---|---|---|
| 1,321,462 | 11/1919 | Line | 219/549 |
| 1,642,197 | 9/1927 | Fowler | 219/549 |
| 2,543,297 | 2/1951 | Olmsted | 219/389 |
| 3,057,183 | 10/1962 | DeFord | 55/197 |
| 3,152,313 | 10/1964 | Barbour | 219/549 |
| 3,319,351 | 5/1957 | Sprissler | 219/389 |
| 3,859,209 | 1/1975 | Jahnsen | 55/67 |
| 3,901,656 | 8/1975 | Durkos | 23/230 B |
| 3,944,651 | 3/1976 | D'Souza | 219/389 |
| 4,237,733 | 12/1980 | Kolb | 73/423 A |
| 4,281,238 | 7/1981 | Noma | 219/549 |

FOREIGN PATENT DOCUMENTS

| | | | |
|---|---|---|---|
| 0071092 | 2/1983 | European Pat. Off. | 422/89 |
| 1297904 | 6/1969 | Fed. Rep. of Germany. | |
| 116102 | 8/1926 | Switzerland | 219/535 |

Primary Examiner—C. L. Albritton
Assistant Examiner—Teresa J. Walberg
Attorney, Agent, or Firm—E. T. Grimes; F. L. Masselle; J. D. Crane

[57] ABSTRACT

A sample vessel container in a sampling device for use in gas chromatography includes a rotatable metal block having a circular array of axial bores for accommodating a plurality of sample vessels. A heating jacket operative as an electric heater is non-rotatably connected to a housing, which jacket tightly surrounds in material contact with, and is adapted to heat, the rotatable metal block.

4 Claims, 4 Drawing Figures

ELECTRIC HEATER FOR A ROTATING SAMPLE VESSEL CONTAINER IN A SAMPLING DEVICE FOR GAS CHROMATOGRAPHY

BACKGROUND OF THE INVENTION

The present invention generally relates to an electric heater for a rotating sample vessel container in a sampling device for gas chromatography and, in particular, relates to an electric heater which is stationary with respect to the rotating sample vessel container.

The sampling device is preferably of the type wherein a capillary connecting conduit formed as a needle is connected to the inlet of the separating column for the purpose of withdrawing samples from sample vessels which are closed by self-sealing membranes. A controllable valve is arranged in a carrier gas conduit leading to the inlet of the separating column. The valve may be closed for the purpose of sample feeding. The sampling device includes a table mounted on an axle and thermally controlled means for accommodating a plurality of sample vessels are provided such that each of the sample vessels is positionable under the stationary needle. Together the table and sample vessels are axially movable upwards in the direction towards the needle, whereby the sample vessel is pushed up on the needle such that the needle pierces the membrane.

One sampling device is known from German Auslegeschrift No. 1 297 904. In such sampling devices vapor from the head space above a sample enclosed in a sample vessel by means of a self-sealing membrane is supplied to the gas chromatograph. In the sample vessel closed by the membrane a state of equilibrium exists such that, in the head space above the sample, the different sample components are present with partial pressures, which are representative of the composition of the sample. A sample component, which is contained in high concentration in the sample, has a high partial pressure in the state of equilibrium in the head space. To obtain unambiguous results, the sample has to be maintained at a well-defined, relatively high temperature.

A sampling device for gas chromatographs is known from German Auslegeschrift No. 1 297 904. Therein, a turntable accommodating the sampling devices includes a thermostatized liquid bath. The sample vessels are inserted into the liquid bath from above. The liquid of the liquid bath evaporates. The turntable, which is rotatable relative to the liquid bath, is supported on a sealing ledge provided at the edge of the liquid bath. Furthermore, the liquid bath and the edge of the turntable accommodating the sample vessels are provided with a covering which is screwed on at the edge of the liquid bath. The covering is provided with arcuate openings through which the sample vessels can be inserted into the turntable. These openings are adapted to be closed by detachable lids. This arrangement is complicated in construction and manipulation.

German Offenlegungsschrift No. 22 44 260 discloses a device for preparing a series of sample preparations of physiological liquids with a transporting disc. Therein the device intended for increasing the temperature is provided in the area of the transporting disc. Sample vessels are guided in a holding groove extending along the circumference of the transporting disc. A heating liquid from a container is pumped through a heating device into the holding groove and exits via an overflow back into the container. Thus, the heating liquid flows around the sample vessels. Temperature sensors are arranged in the holding groove, by which the heating is controlled.

This is a sampling device for gas chromatographs with a turntable arranged to be lifted against a needle. Also, a liquid bath is provided as the thermostatizing means, only the liquid bath is heated and regulated in circulation. This circulation heater is expensive. Further, it is difficult to pass such a circulation through a rotatable turntable arranged to be lifted axially, as it is required in a sampling device of the above-mentioned type. In addition, when using a liquid bath the temperature range is limited by the boiling temperature of the liquid.

In German Offenlegungsschrift No. 28 18 251 an electrically heated metal block is provided as a thermostatizing means for the sample vessels. Therein, the metal block is rotatably mounted about a non-rotatable axle and has a circular array of axial through-bores with the axle as center. A base plate is non-rotatingly connected to the axle and closes the axial through-bores towards the bottom.

A closable aperture, allows for the insertion of a sample vessel into respective axial throughbores aligned with the aperture, is provided in the base plates such that the sample vessels can be inserted into the heated metal block by turning it. The axle with the base plate and the metal block is arranged to be moved in axial direction such that this axle is axially movable in the direction towards the needle.

The thermally controlled means, in the form of an electrical heater, includes an electric heating coil fixed to the metal block and is thus arranged to rotate therewith. Thus, the heating power in the form of electrical energy has to be transferred to the heating coil through sliders, which transference is disadvantageous in operational efficiency as well as being expensive to construct.

SUMMARY OF THE INVENTION

Accordingly, it is one object of the present invention to simplify, with regard to the current supply, the electric heating of a rotatable sampling device by a stationary heating coil.

This object is achieved, at least in part, by providing a heating jacket operative as an electric heater which is non-rotatingly connected to a housing but which tightly surrounds and is in material contact with a rotatable metal block.

Other objects and advantages will become apparent to those skilled in the art from the following detailed description read in conjunction with the appended claims and the attached drawing.

BRIEF DESCRIPTION OF THE DRAWINGS

An embodiment of the present invention is described hereinafter in greater detail with reference to the accompanying drawing, not drawn to scale, and in which.

DETAILED DESCRIPTION OF THE INVENTION

Figure 1:
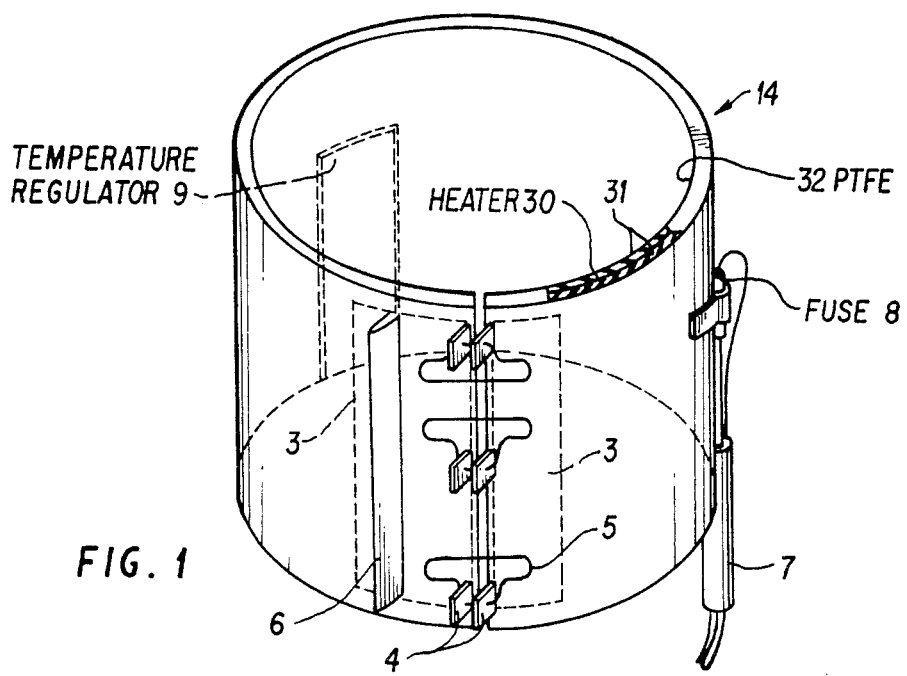
FIG. 1 is a perspective view of a heating jacket embodying the principles of the present invention.
Figure 2:
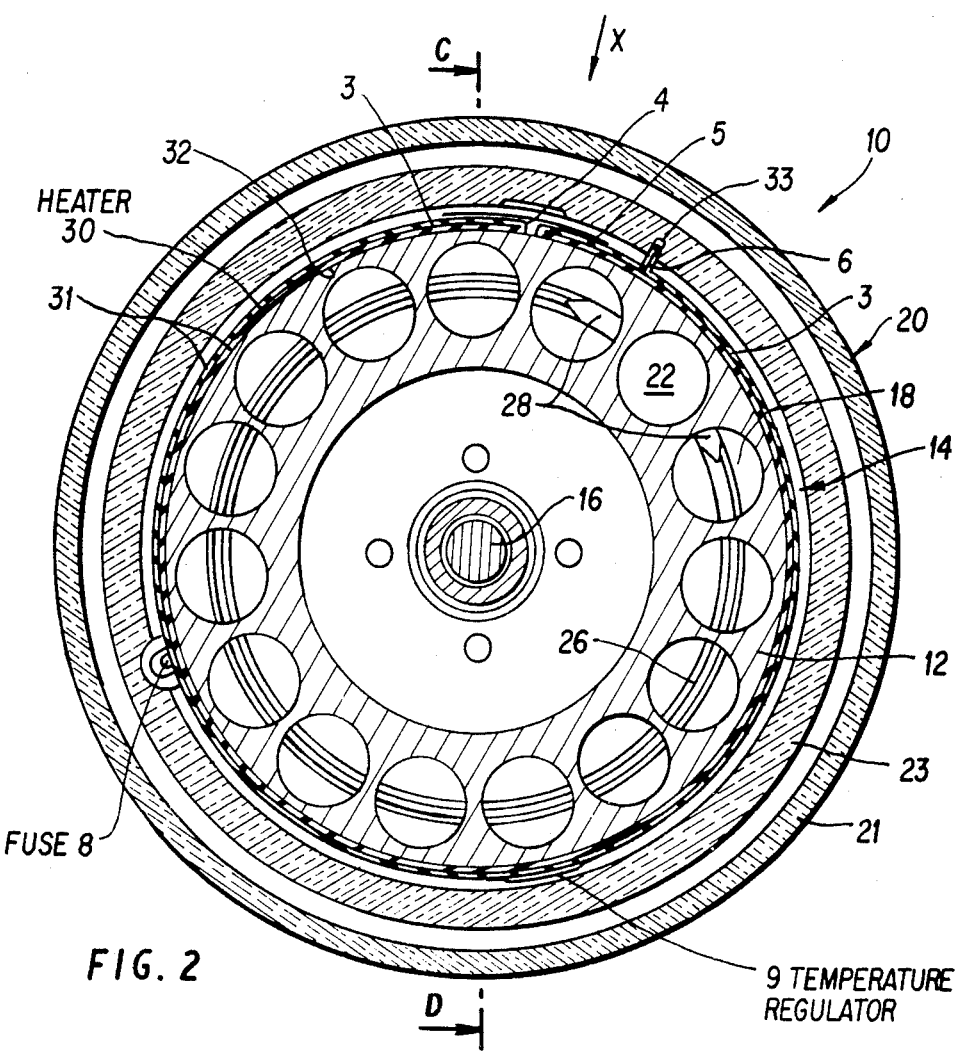
FIG. 2 is a cross-sectional view of a sampling incorporating the heating jacket shown in FIG. 1.
Figure 3:
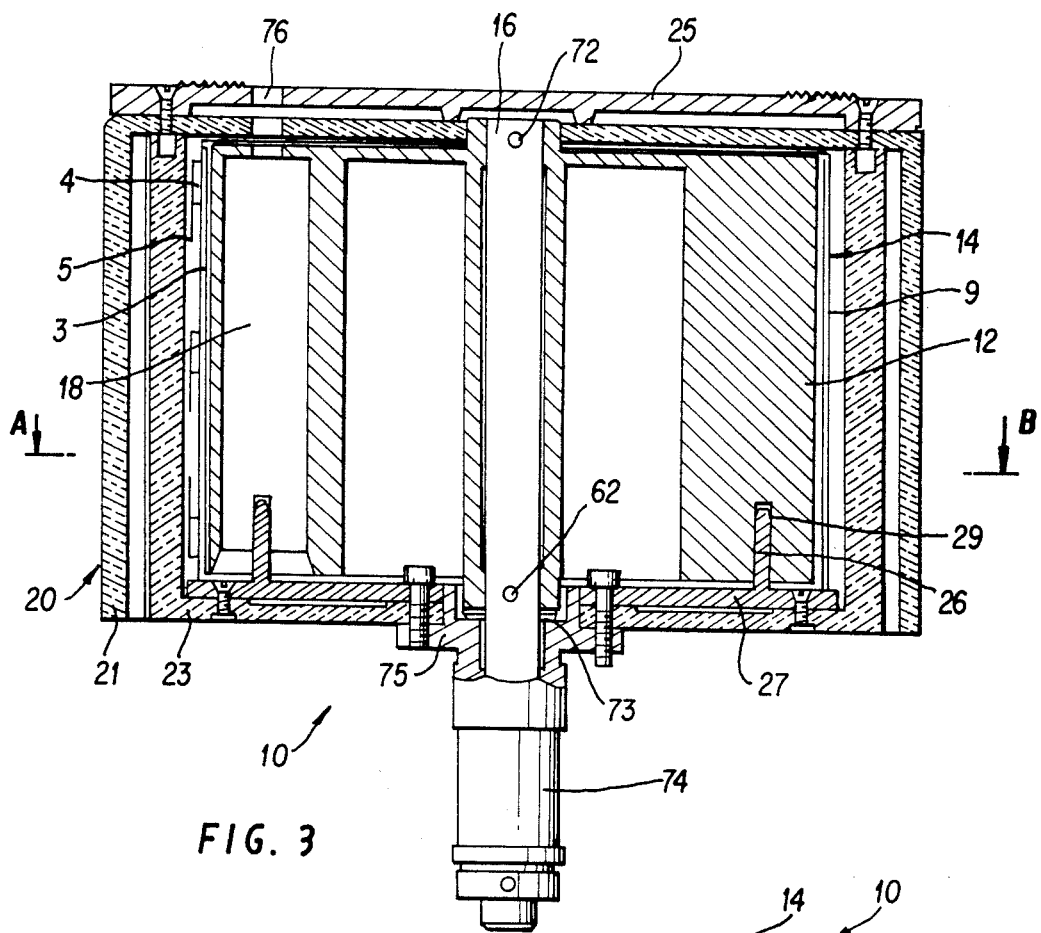
FIG. 3 is a sectional view taken along the line 3—3 of FIG. 2.
Figure 4:
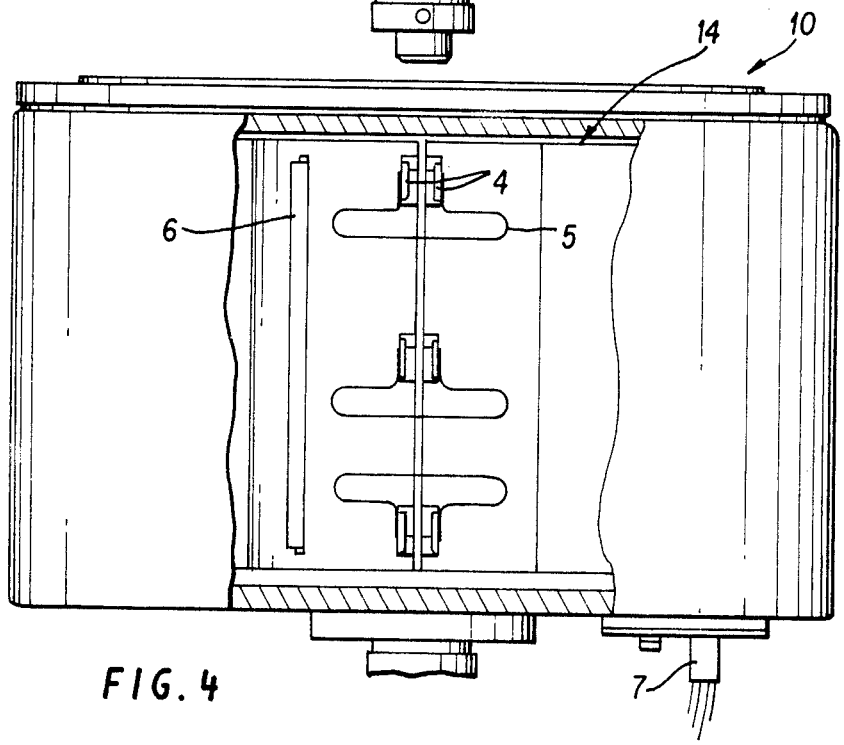
FIG. 4 is a partial sectional view of the sampling device shown in FIG. 2 as viewed from the direction represented by the arrow designated by X.

A sample carrier, generally indicated at 10, in the drawing, includes as a thermally controlled means, a metal block 12 adapted to be heated by an electrical heater 14. The metal block 12 is rigid affixed to a rotatable shaft 16 by, for example, two transverse pins, 62 and 72, and includes therein a circular array of axial throughbores 18. The shaft 16 is rotatably mounted in a sleeve 74 and serves as the axis for the circular array of axial throughbores 18.

A housing 20 is affixed to a flange 75 of the sleeve 74 by, for example, screws. The housing 20 includes two interconnected cup-shaped housing parts, 21 and 23, one housing part 23 being positioned within the other housing part 21. The housing 20 also includes a cover 25 and a disc 27, the disc 27 is provided with an annular ledge 26 which extends upwardly therefrom. In operation, the ledge 26 engages a radially annular slot 29 of the metal block 12 and supports the sample vessels inserted into the axial throughbores 18 in position. The throughbores 18 containing the sample vessels are charged through an aperture 22 in the cup-shaped housing part 23, through which aperture 22 a respective sample vessel can be inserted into an axial throughbore 18 aligned with the aperture 22.

Upon rotating the shaft 16 the metal block 12 is rotated relative to the housing 20 such that the sample vessels are lifted and brought into position through inclined surfaces 28 provided on the annular ledge 26. The cover 25 and the cup-shaped housing part 21 include openings which are aligned to define an aperture 76 for the passage of a needle.

The heater jacket 14 includes an electric heating coil 30 which is sandwiched between two silicone mats 31. The jacket 14 cylindrically surrounds the metal block 12 and is in thermal communication therewith via the inner silicone mat 31. The inner side of the cylindric heating coil 30 proximate the metal block 12 is preferably provided with a layer 32 of material having minimal friction resistance, such as, for example, polytetrofluroethelene (PTFE). The heater 14 tightly engages, as is in material contact with the metal block 12. Hence when the metal block 12 is rotated about the shaft 16 relative to the heater 14 the PTFE layer 32 reduces the frictional forces therebetween while nevertheless maintaining a thermal transfer relation between the coil 30 and the metal block 12.

The silicone mats 31 with the heating coil 30 therebetween is placed around the metal block 12. Preferably, this jacket 14 is secured about the metal block 12 by a metal strap 3 which strap can be vulcanized thereonto at their ends thereof to form a plurality of longitudinal slots. Each of the metal straps 3 includes three sets of brackets 4 bent at a right angle with respect to the surface of the cylinder. That is, the brackets 4 extend radially outwardly from the jacket 14. In the preferred embodiment bow springs 5 are provided to engage recesses in the brackets 4 at two opposing brackets each and thereby stretch the heating jacket 14 about the metal block 12. The jacket is also provided with an elongated anti-rotating means 6 extending outwardly at a right angle. The means 6 is preferably additionally arranged on any one of the straps 3 and secures the heating jacket 14 against rotation relative to the housing 20 by engaging a longitudinal groove 33 formed in the fixed cup-shaped part 23 of the housing 20.

The heating coil 30 is supplied with power through a current supply 7 which, preferably, includes a fire safety fuse 8. The heating power is controlled and adjusted through a temperature regulator 9.

The present invention has been described herein by means of an exemplary embodiment. Other arrangements and configurations may be made by those skilled in the art which do not depart from the spirit and scope of this invention. Hence, the present invention is deemed limited only by the appended claims and the reasonable interpretation thereof.

What is claimed is:

1. A sampling device comprising:
   a rotatable sample vessel container for accommodating a plurality of sample vessels, means for selectively moving each of said sample vessels to a sample feeding position;
   an electric heater for heating said container;
   a housing, said container being positioned in said housing;
   a heating jacket positioned between said container and said housing, said jacket surrounding said container; said jacket including an electric heating coil enclosed between two silicone mats;
   means for maintaining said jacket in material contact with said container whereby a thermal transfer relation is maintained therebetween and;
   means between said jacket and said housing for preventing rotation of said jacket.

2. A sampling device comprising:
   a rotatable sample vessel container for accommodating a plurality of sample vessels, means for selectively moving each of said sample vessels to a sample feeding position;
   an electric heater for heating said container;
   a housing, said container being positioned in said housing;
   a heating jacket positioned between said container and said housing, said jacket surrounding said container;
   means for maintaining said jacket in material contact with said container whereby thermal transfer relationship is maintained therebetween;
   the radially inner surface of said jacket being coated with PTFE whereby frictionally forces between said container and said heating jacket are reduced; and
   means, between said jacket and said housing, for preventing rotation of said jacket.

3. A sampling device comprising:
   a rotatable sample vessel container for accommodating a plurality of sample vessels, means for selectively moving each of said sample vessels to a sample feeding position;
   an electric heater for heating said container;
   a housing, said container being positioned in said housing;
   a heating jacket positioned between said container and said housing, said jacket surrounding said container;
   means for maintaining said jacket in material contact with said container whereby a thermal transfer relationship is maintained therebetween and;
   means, between said jacket and said housing, for preventing rotation of said jacket, said jacket including an electric heating coil enclosed between two silicone mats, metal straps being affixed to said silicone mat proximate said housing, which straps including brackets formed at right angles and functioning to stretch said heating jacket about said container by means of bow strings.

4. A sampling device as claimed in claim 3 wherein said jacket rotation preventing means includes a metal protrusion affixed to said silicone mat proximate said housing, and said housing having a slot for accepting said metal protrusion.

* * * * *